US00PP23553P2

(12) United States Plant Patent
Kordes

(10) Patent No.: US PP23,553 P2
(45) Date of Patent: Apr. 23, 2013

(54) HYBRID TEA ROSE PLANT NAMED 'KOR052700'

(50) Latin Name: *Rosa hybrida*
Varietal Denomination: KOR052700

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 13/136,639

(22) Filed: Aug. 5, 2011

(51) Int. Cl.
*A01H 5/00* (2006.01)

(52) U.S. Cl. ..... Plt./137

(58) Field of Classification Search ..... Plt./137, Plt./138, 139, 140
See application file for complete search history.

*Primary Examiner* — Kent L Bell

(57) ABSTRACT

A new and distinct variety of rose with long lasting, novel pink flowers, and attractive foliage with good disease resistance. It exhibits vigorous growth and an upright to bushy habit with abundant flowers. The new variety propagates well by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KOR052700'.

CROSS REFERENCES AND FEDERAL R&D STATEMENT

There are no cross referenced or related applications. This variety was developed without the aid of any research grant.

BACKGROUND OF THE INVENTION

The present discovery constitutes a new and distinct variety of a cut flower rose plant which was discovered in a cultivated area at the inventor's nursery in Offenseth-Sparrieshoop in May, 2005. The new rose variety resulted from a naturally occurring mutation of unknown causation on a branch of 'KORtiglo', a patented rose described and illustrated in U.S. Plant Pat. No. 19,385, and issued on Oct. 28, 2008.

The new rose plant was asexually propagated for evaluation. This new and distinctive garden rose variety is named 'KOR052700'.

SUMMARY OF THE INVENTION

The new rose plant may be distinguished from 'KORtiglo', by the following combination of characteristics:

1. The fragrance of 'KOR052700' is strong while the fragrance of 'KORtiglo' is light.
2. The general tonality on an open flower of 'KOR052700' is Red Group 49B while the general tonality of 'KORtiglo' is Yellow-Orange Group 20C.

The new and distinct rose plant was selected due it its':

1. Uniform growth and flowering;
2. Abundant attractive, recurrent flowers;
3. Attractive and abundant foliage; and
3. Resistance to diseases encountered in commercial outdoor cut flower production.

This combination of qualities is not present in prior rose cultivars known to the inventor. These objectives have been substantially achieved and in that distinguish 'KOR052700' from all other varieties of which I am aware.

As part of the rose development program, Tim-Hermann Kordes asexually propagated the mutation by grafting and conducted evaluations and observations on the resulting plants in the inventor's nursery in Offenseth-Sparrieshoop, Germany. The first asexual propagation of 'KOR052700' was done by budding to seedling understocks in June, 2005 at the inventor's nursery in Offenseth-Sparrieshoop, Germany.

This initial and other subsequent propagations conducted in controlled environments demonstrate that 'KOR052700' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, flowers, leaves, and stems of 'KOR052700'.

DETAILED BOTANICAL DESCRIPTION

The following is a description of 'KOR052700', as observed growing July, 2011 in a nursery in Jackson County, Oreg. on plants of 3 years of age. Color references are made using The Royal Horticultural Society (London, England) Colour Chart, 2001 except where common terms of color are used.

For a comparison, several physical characteristics of the rose variety 'KOR981457', a rose variety from the same inventor are compared to 'KOR052700' in Chart 1.

CHART 1

| Characteristic | 'KOR052700' | 'KOR981457' |
|---|---|---|
| Average flower bud size: | 30-35 mm in length and 23-26 mm in diameter. | 28 mm in length and 23 mm in diameter. |

CHART 1-continued

| Characteristic | 'KOR052700' | 'KOR981457' |
|---|---|---|
| General tonality of flower: | Red Group 49B. | Red-Purple Group 62D. |
| Fragrance: | Strong. | Strong. |

Parents:

*Parent*.—'KORtiglo'.

Classification:

*Botanical classification*.—*Rosa hybrida* 'KOR052700'.

*Commercial classification*.—Hybrid Tea rose.

FLOWER AND FLOWER BUD

Blooming habit: Recurrent.

Flower bud:

*Size*.—Upon opening, 30-35 mm in length from base of receptacle to end of bud and 23-26 mm diameter at its widest point.

*Bud form*.—Short and globular.

*Bud color*.—As sepals first unfold, bud color is Red Group 47D. When ¼ open, the upper surface of petals is a blend of Red Group 37A, Orange-Red Group 32C, and Red-Grey Group 36A. The basal area color is Yellow Group 12A. The lower surface is a blend of Red Group 37A, Orange-Red Group 32C, and Red-Grey Group 36A with the basal area Yellow Group 12A. The guard petals are Red Group 48B with center stripe Orange Group Yellow Group 2C.

*Sepals*.—Size: Average 25-30 mm long×8-10 mm wide. Color: Upper surface Yellow-Green Group 146C with intonations of Greyed-Red Group 182D. Lower surface is Yellow-Green Group 144A. Shape: Weak foliaceous appendages on two of the five sepals. Apex: Apiculate. Base: Flat at union with receptacle. Quantity: Five. Margins: Cirrose with stipitate glands. Surface texture: Inner side: Pubescent. Outer surface: Lightly pubescent.

Receptacle:

*Surface*.—Cirrose, with stipitate glands.

*Color*.—Yellow-Green Group 144B.

*Shape*.—Funnel-shaped.

*Size*.—10 mm (h)×15 mm (w).

Peduncle:

*Surface*.—With fine hairs and stipitate glands.

*Length*.—110 to 140 mm average length.

*Diameter*.—4 to 5 mm average diameter.

*Color*.—Yellow-Green Group 146C.

*Strength*.—Strong.

*Borne*.—Multiple flower buds per stem, generally 3 to 5.

Flower bloom:

*Fragrance*.—Strong.

*Duration*.—On the plant 10-12 days. Long lasting. As a cut flower, 10-12 days. Senesced petals drop away cleanly.

*Size*.—Medium sized for an Hybrid Tea rose. When open, the average flower diameter is 110-120 mm and the average flower height is 40-50 mm.

*Form*.—Shape of flower when viewed from the side: Upon opening, upper part: Flattened convex. Upon opening, lower part: Concave. Open flower, upper part: Flattened convex. Open flower, lower part: Concave.

Color:

*Upon opening, petals*.—Outermost petals: Outer Side: Middle and marginal zones are a blend of Orange-Red Group 50B and Orange-Red Group 35D. The basal zone is Yellow Group 13B. Inner Side: Middle and marginal zones are a blend of Orange-Red Group 50B, Orange-Red Group 35D. The basal zone is Yellow Group 13B. Innermost petals: Outer Side: Orange-Red Group 31B with a center stripe of Yellow Group 13B. Inner Side: Orange-Red Group 32B.

*Upon opening, basal petal spots*.—Basal petal spot, outermost petals: Outer Side: Yellow Group 2A. Inner Side: Yellow Group 2A. Basal petal spot, innermost petals: Outer Side: Yellow Group 13A. Inner Side: Yellow Group 13A.

*After opening, petals*.—Outermost petals: Outer Side: Red Group 49C. Inner Side: Red Group 49B with basal zone of Yellow Group 9D. Innermost petals: Outer Side: Red-Purple Group 62B with basal zone Yellow Group 9D. Inner Side: Red-Purple Group 62C.

*After opening, basal petal spots*.—Basal petal spot, outermost petals: Outer Side: Yellow Group 7C. Inner Side: Yellow Group 9D. Basal petal spot, innermost petals: Outer Side: Yellow Group 8C. Inner Side: Yellow Group 8B.

General tonality: On open flower Red Group 49B. No change in the general tonality at the end of the $8^{th}$ day. Afterwards, general tonality is Red Group 49C.

Petals:

*Petal count*.—Approximately 100 petals under normal conditions.

*Petal reflex*.—Petals reflex slightly.

*Petal edge*.—Mucronate.

*Petal shape*.—Obovate. Apex shape is obtuse. Shape of base is deltoid.

*Petal size*.—30-50 mm (l)×20-30 mm (w).

*Thickness*.—Thick.

*Petal arrangement*.—Rosetted.

Petaloids: Present.

*Petaloid count*.—Average of 15-25 per flower.

*Petaloid size*.—Petaloids are 10-15 mm (l) and 8-12 mm (w).

*Petaloid color*.—Color of inner side is Red Group 38B. Color of outer side is Red Group 38D.

*Petaloid texture*.—Smooth.

*Margins*.—Entire.

*Petaloid shape*.—Entire petaloid: Irregular. Obovate to subulate. Apex: Irregular. Obovate to acute. Base: Acute.

Reproductive organs:

*Pistils*.—Approximately 50-60 present. Stigmas: Location: Slightly inferior in position to anthers. Color: Green-Yellow Group 160C with intonations of Red Group 39C. Styles: Length: About 5 mm long. Color: Yellow-Green Group 145C. Intonations of Red Group 45C.

*Stamens*.—Approximately 75-100 on average and regularly arranged. Anthers: Size: About 0-5 mm long. Pollen: Generally present. Color: Brown Group 200C. Filaments: Color: Yellow Group 7C. Length: Approximately 4-5 mm.

THE PLANT

Growth: Vigorous.

Plant habit: Upright to bushy habit. When grown as a budded field grown plant, the average plant height is 130 cm and the average plant width is 50 cm.

Stems:

*Stem color*.—Juvenile stems: Yellow-Green Group 146C. Mature stems: Yellow-Green Group 146C.

*Stem surface*.—Juvenile stems: Smooth. Mature stems: Rough with numerous prickles and stipitate glands.

Prickles: Present.

*Incidence*.—8 per each 10 cm of stem.

*Size*.—Average length: 5-7 mm.

*Color*.—Immature prickles: Yellow-Green Group 146D. Mature prickles: Greyed-Yellow Group 162C. Senescing to Greyed-Orange Group 177B.

*Anthocyanin*.—Color Greyed-Orange Group 176B.

*Shape*.—Concave.

Leaves and leaflets: Normally 5 leaflets on normal leaves in middle of the stem.

*Venation pattern*.—Pyramidal net pattern.

*Leaf size*.—120-130 mm (l)×90-110 mm (w).

*Quantity*.—Average.

*Texture*.—Thick. Upper side of leaflet: Semi glossy and smooth. Under side of leaflet: Matte and smooth.

*Color, mature foliage*.—Upper Leaf Surface: Green Group 139A. Lower Leaf Surface: Yellow-Green Group 147B.

*Color, juvenile foliage*.—Upper Leaf Surface: Yellow-Green Group 146A. Lower Leaf Surface: Yellow-Green Group 146D.

*Anthocyanin intonation*.—Present. Intonations of Greyed-Purple Group 183A and 183B present on upper and lower surfaces of juvenile foliage.

Stipules:

*Size*.—15-20 mm long. 5-6 mm between the tips of the stipules.

*Stipule color*.—Yellow-Green Group 144A. Intonations of Greyed-Purple Group 183B on margins and upper side of juvenile foliage.

*Margins*.—With stipitate glands.

*Shape*.—Apex: Apiculate. Base: Flat.

Petiole:

*Length*.—About 12-16 mm.

*Diameter*.—About 2 mm.

*Petiole color*.—Yellow-Green Group 146A.

*Underneath*.—Prickles and stipitate glands.

*Margins*.—With stipitate glands.

Petiole rachis:

*Length*.—About 10-14 mm.

*Diameter*.—About 2 mm.

*Color*.—Yellow-Green Group 146A.

*Underneath*.—With prickles and stipitate glands.

*Margins*.—With stipitate glands.

Leaflets:

*Size*.—Average size of the terminal leaflet is 50-60 mm (l)×30-36 mm (w).

*Shape*.—Entire leaflet: Ovate. Base: Obtuse. Apex: Cuspidate.

*Margins*.—Finely serrated.

*Texture*.—Coriaceous.

Hips/seed formation: None observed.

Winter hardiness: To date, the variety has been grown successfully in USDA Zones 5-9.

Disease resistance: Good resistance to powdery mildew (*Sphaerotheca pannosa*), rust (*P. disciflorum*), and black-spot (*Diplocarpon rosae*), diseases under normal growing conditions.

I claim:

1. A new and distinct variety of rose plant, as described and illustrated herein.

* * * * *

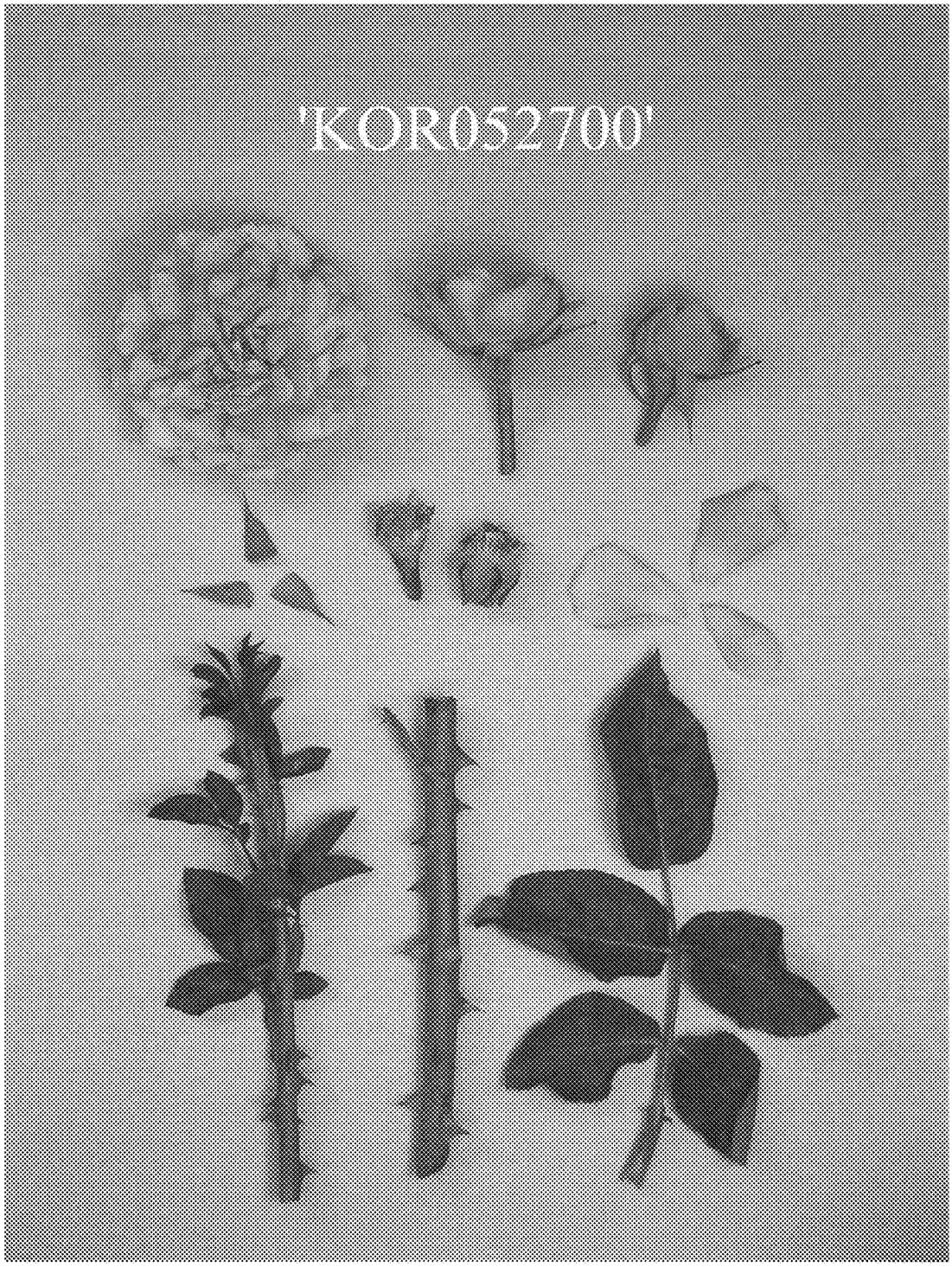
'KOR052700'